United States Patent
Cattani

(10) Patent No.: US 7,326,282 B2
(45) Date of Patent: Feb. 5, 2008

(54) CONTROL DEVICE FOR FLUID SEPARATORS IN DENTAL ASPIRATION PLANTS

(75) Inventor: Ennio Cattani, Parma (IT)

(73) Assignee: Cattani S.p.A., Parma (IT)

( * ) Notice: Subject to any disclaimer, the term of this patent is extended or adjusted under 35 U.S.C. 154(b) by 407 days.

(21) Appl. No.: 10/988,697

(22) Filed: Nov. 16, 2004

(65) Prior Publication Data

US 2005/0109212 A1  May 26, 2005

(30) Foreign Application Priority Data

Nov. 20, 2003  (EP)  .................... 03425747

(51) Int. Cl.
  *B01D 19/00*  (2006.01)
(52) U.S. Cl. .............. 96/156; 96/173; 96/174; 96/204; 96/397; 433/92
(58) Field of Classification Search .......... 95/14, 95/15, 19, 24; 433/92; 96/155, 156, 157, 96/173, 174, 397, 420, 421, 204; 432/92
See application file for complete search history.

(56) References Cited

U.S. PATENT DOCUMENTS 4,842,478 A * 6/1989 Durr et al. ............... 415/169.2

FOREIGN PATENT DOCUMENTS

| DE | 101 12 411 | | 9/2002 |
| DE | 10112411 A1 | * | 9/2002 |
| EP | 0 960 605 | | 12/1999 |

* cited by examiner

*Primary Examiner*—Robert A. Hopkins
(74) *Attorney, Agent, or Firm*—Young & Thompson

(57) ABSTRACT

The control device for a separator includes: a drainage pump powered by a first electric motor and an aspiration pump powered by a second electric motor. It further includes: sensor elements of known type for detecting operating parameters of the separator, such as pressure of liquid in outlet, ambient temperature, motor temperature, and for providing command signals which are proportional to the operating parameters and which command the inverters which upon receiving the command signals modify a frequency of the electrical supply current to the first electric motor and to the second electric motor.

8 Claims, 1 Drawing Sheet

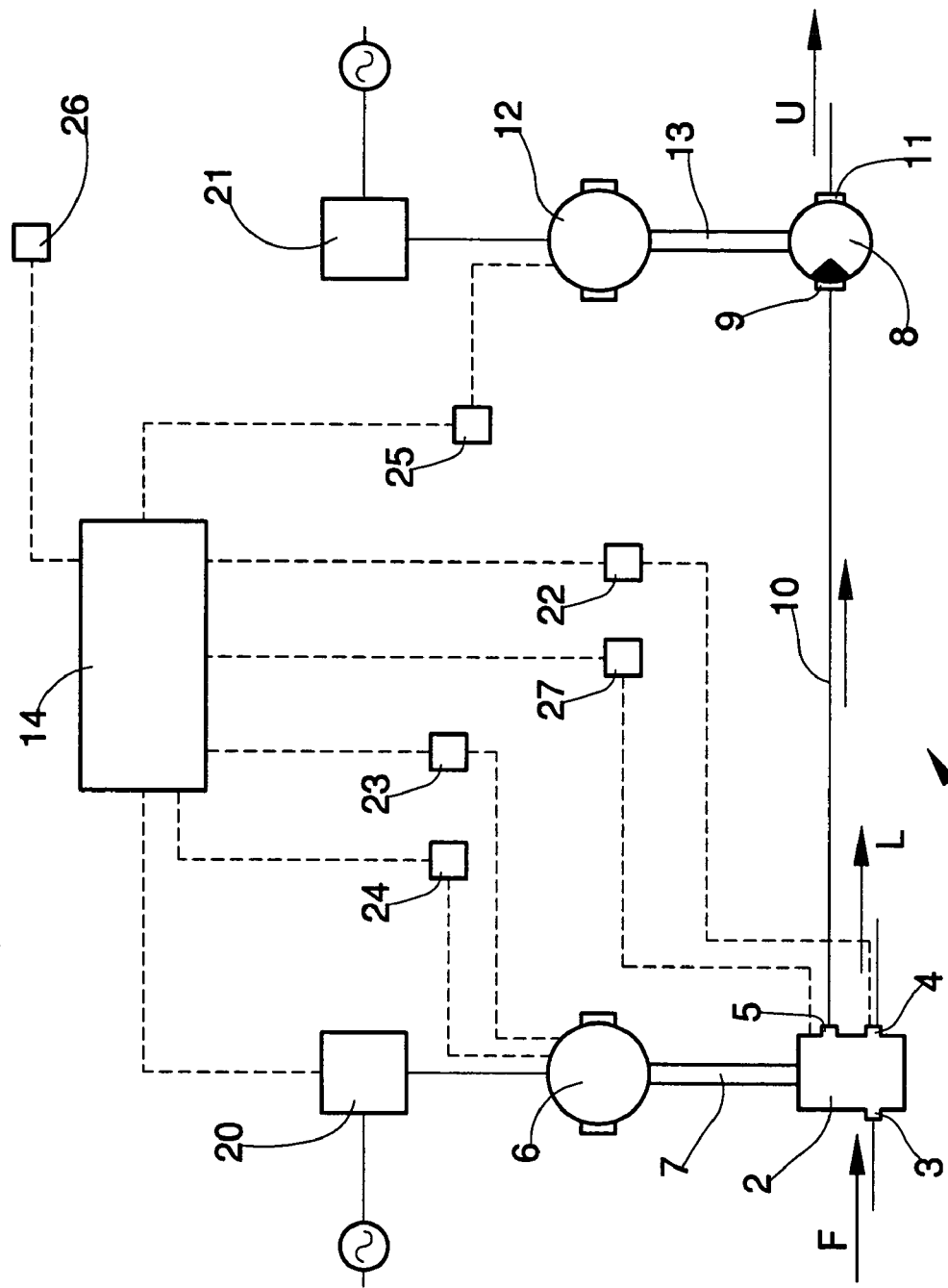

CONTROL DEVICE FOR FLUID SEPARATORS IN DENTAL ASPIRATION PLANTS

BACKGROUND OF THE INVENTION

The invention relates to a fluid separator for dental aspiration apparatus.

The prior art in this field teaches dental apparatus which remove fluids from a patient's mouth during an operation. These fluids comprise a gaseous part and a liquid part. The gaseous part is generally air, while the liquid part is usually composed of water, organic liquids and other liquids used in dental apparatus. The gaseous part has to be separated from the liquid part before the latter is purified and ultimately discharged into the sewers. The prior art teaches separators for this purpose, which combine the action of a centrifuge drainage pump with that of a suction pump. In these separators the fluids which are to be separated are sent into the centrifuge pump; the suction pump creates a depression inside the centrifuge pump causing the gaseous part of the fluid to be aspirated by the suction pump, while the liquid part exits through an aperture afforded in the centrifuge pump. The prior art teaches separators, for example European publication EP 0 960 605 by the same applicant, in which the centrifuge pump and the suction pump are activated by separate motors.

The use of separate motors has solved some problems which can emerge during the halting stage and the restart stage of the plant. In particular, by use of timers for regulating the start-up of one motor in relation to the start-up of the other, it is possible to avoid infiltration of liquid into the suction pump. During operation of the plants sometime undesired events occur, such as, for example, excessive increase of outletting liquid pressure from the separator, with a consequent increase in the liquid level in the drainage pump and the possibility of aspiration of liquid by the suction pump, or a too-high operating temperature in the drainage pump, due both to excessive absorption of current by the motors and to an increase in ambient temperature to above admissible levels. In these cases it is often necessary to halt the plant, a step which is not at all appreciated by the users of the plants.

The main aim of the invention to obviate the above-mentioned drawbacks by providing a control device which enables an optimisation of the functioning parameters of the plant and obviates any undesired operating conditions, without having recourse to the need to shut the plant down.

An advantage of the invention is that it enables regulation, at a desired value, of the degree of depression produced by the suction pump, independently of the quantity of fluid aspirated, i.e. independently of the number of operators using the plant at the same time.

A further advantage of the invention is that it optimises the electrical power needed to operate the motors according to the demand placed by the users of the separator.

These aims and advantages and more besides are all attained by the present invention, as it is characterised in the appended claims.

SUMMARY OF THE INVENTION

The control device for a separator of the invention comprises: a drainage pump powered by a first electric motor and an aspiration pump powered by a second electric motor. It further comprises: sensor means of known type for detecting operating parameters of the separator, such as pressure of liquid in outlet, ambient temperature, motor temperature, and for providing command signals which are proportional to the operating parameters and which command the inverters which upon receiving the command signals modify a frequency of the electrical supply current to the first electric motor and to the second electric motor.

BRIEF DESCRIPTION OF THE DRAWINGS

Further characteristics and advantages of the present invention will better emerge from the detailed description that follows of a preferred but non-exclusive embodiment of the invention, illustrated purely by way of a non-limiting example in the accompanying figure of the drawing, in which:

FIG. 1 is a diagram of a separator made according to the invention.

DESCRIPTION OF THE PREFERRED EMBODIMENTS

With reference to the figure of the drawing, 1 denotes in its entirety a separator for dental aspiration plants. The separator 1 comprises a centrifuge drainage pump 2 provided with an inlet 3 for the fluid to be separated. The fluid enters the centrifuge pump 2 in the direction indicated by the arrow F of FIG. 1. The drainage pump 2 is further provided with an outlet 4 for the liquids exiting from the drainage pump 2 in the direction indicated by the arrow L of FIG. 1, to be sent on to discharge into the drains. The drainage pump 2 also exhibits an air outlet hole 5. The drainage pump 2 is actuated by a first electric motor 6, having a drive shaft 7 coaxially bearing the drainage pump 2 impeller.

The separator 1 comprises a suction pump 8, predisposed for creating a predetermined degree of depression in the separator and for extraction of gases from the fluid introduced into the separator 1. The suction pump 8 is provided with an inlet 9 for the air, which inlet 9 is connected, through a conduit represented schematically in FIG. 1 and denoted by 10, with the outlet 5 of the drainage pump 2. The suction pump 8 is further provided with an outlet 11 for the air, through which the aspirated air is evacuated in the direction indicated by the arrow U in FIG. 1. The separator 1 also comprises a second motor 12, distinct from the first motor 6, which sets the suction pump 8 impeller in rotation by means of a shaft 13. Thus each motor 6 and 12 sets a respective pump 2 and 8 in rotation.

The above description is known from European publication EP 0 960 605. The separator is provided with a control device comprising sensor means for acquiring values relating to operating parameters of the separator. In particular the device of the invention comprises sensor means as follow:

a first sensor 22 which is connected, for example, to the outlet 4 of the drainage pump 2 and which monitors the liquid pressure at the outlet of the drainage pump 2;

a second sensor 23 which monitors the supply current to the motor 6 of the drainage pump 2;

a third sensor 26 which monitors the ambient temperature in the place where the separator is located;

a fourth sensor 24 and a fifth sensor 25, each of which monitors the temperatures, respectively of the motor 6 and the motor 12;

a sixth sensor 27 which detects the degree of depression (i.e. the pressure) inside the separator 1.

All of the above sensors are of widely known type and normally used, and each provides a command signal which is proportional to the value of the operating parameter of the separator which each of them monitors.

The device of the invention further comprises means for electrical supply, of known type, which are commanded by command signals generated by the above-described sensors and which can modify the frequency of the electric supply current to the first electric motor 6 or the second electric motor 12, or both motors 6 and 12.

The means for electrical supply comprise a first inverter 20, which is connected to the first electric motor 6, and a second inverter 21, which is connected to the second electric motor 12.

The inverters 20 and 21 are supplied by the normal electricity supply and provide in output an electric current the frequency of which is not the same as the normal supply current but which is variable according to command signals supplied to the inverters 20 and 21.

The electric motors 6 and 12 are supplied by the variable current in output from the inverters 20 and 21; thus, according to the command signal provided to the inverters 20 and 21 the electricity supply frequency can be varied to the motors 6 and 12, and therefore their rotation velocity can be varied, as it depends on the frequency of the electrical supply.

The device is provided with a central unit 14 of command and control, constituted by a processor card of known type, which receives the signals generated by the sensors and commands the inverters 20 and 21 in order to vary, according to needs, the rotation speed of one or both motors 6 and 12. Each time the sensors detect a fault in normal separator operation, the device intervenes without having to halt separator functioning, and re-establishes the normal operating conditions. In other words, the device enables "balanced" operation of the motors 6 and 12, and the pumps 2 and 8, the rotation speeds of which are independently regulated in relation to one another in order to modify the conditions which led to faulty operation of the separator.

If, for example, the drainage pump 2 is not able to expel all of the liquid through the outlet 4 and shows a tendency to flood (a situation which it is absolutely necessary to avoid as it might lead to an aspiration of liquid by the suction pump 8) the sensor 22 detects an increase in the liquid pressure at the outlet 4 of the pump 2; the signal generated by the sensor 22 is transmitted to the central unit 14 which instructs the inverter 20 to increase the current frequency to the motor 6 in order to increase the revolutions of the pump 2 and to remove the liquid present in the pump 2 more quickly. Alternatively the central unit can command the inverter 22 to lower the frequency of the supply current to the motor 12 so that the pump 8 revolutions are decreased and likewise the quantity of fluid aspirated by the pump is decreased.

If the sensor 23 detects an undesired increase in the intensity of the supply current to the motor 6, a symptom indicating excessive stress on the motor 6, a command signal is generated which is transmitted to the central unit 14, which commands the inverter 21 to reduce the motor 12 supply current frequency in order to reduce the number of revolutions of the pump 8 and accordingly the quantity of fluid aspirated by the pump 2, i.e. the stress on the motor 6.

In cases where the external ambient temperature where the separator is located, or the temperatures of the motors 6 and 12, increase beyond a predetermined limit, the sensors 24, 25, 26 generate command signals which are transmitted to the central unit 14, which commands the inverters 20 and 21 to reduce the frequency of the supply current to the motors 6 and 12, in order to diminish the rotation speed thereof and consequently the overheating thereof.

With the device of the invention a desired degree of depression can be maintained internally of the separator independently of the number of users connected to the separator. The sensor 27 generates a signal which is proportional to the degree of depression present in the separator and sends the signal to a central unit 14 in which the signal is compared with a reference signal. If it is found that there is a difference between the signals, the unit 14 commands the inverter 12 to modify, increasing or lowering according to needs, the frequency of the supply current to the motor 12; thus the revolution count (and degree of aspiration) of the pump 8 is adjusted so that the desired degree of depression can be re-established.

Briefly, the device of the invention optimises the performance of the separator, by acting on the rotation speed of the motors 6 and 12, and therefore the pumps 2 and 8, through the inverters 20 and 21 which modify the frequency of the electric supply current to the motors 6 and 12. This prevents onset of problems connected to faults of various natures or having different operative needs which the separator has to satisfy, with no need however to shut down the separator and without the user or users actually noticing in any significant way the interventions of the device.

The device is also extremely versatile inasmuch as it enables the separator functioning to be adjusted, especially the operation of the motors which separately activate the aspiration pump and the drainage pump, simply and rapidly and on the basis of all the parameters which define the operation of the separator. In this way the separator operation is at all times sufficient to the needs of the users, preventing useless consumption of electric energy.

What is claimed is:

1. A control device for fluid separators in dental aspiration plants, comprising: a drainage pump powered by a first electric motor and provided with an inlet for a fluid to be separated, a first outlet for liquids and a second outlet for gases; an aspiration pump powered by a second electric motor and provided with an inlet for the gases connected to the second outlet of the drainage pump; sensor means for detecting operating parameters of the separator and for providing command signals which are proportional to the operating parameters; and means for electrical supply commanded by the command signals and adapted to modify a frequency of the electrical supply current to the first electric motor and to the second electric motor.

2. The device of claim 1, wherein the means for electrical supply comprise at least one inverter of known type.

3. The device of claim 2, wherein the means for electrical supply comprise a first inverter which is connected to the first electric motor and a second inverter which is connected to the second electric motor.

4. The device of claim 1, which further comprises a first sensor which detects a pressure of the liquid at the first outlet of the drainage pump and provides one of the command signals.

5. The device of claim 1, which further comprises a second sensor which detects an entity of a supply current to the motor of the drainage pump and provides one of the command signals.

6. The device of claim 1, which further comprises a third sensor which detects an ambient temperature in a place where the separator is located and provides one of the command signals.

7. The device of claim 1, which further comprises a fourth sensor and a fifth sensor, each of which detects a temperature of one of the first and second electric motors and provides one of the command signals.

8. The device of claim 1, which further comprises a sixth sensor which detects a degree of depression inside the separator and provides one of the command signals.

* * * * *